United States Patent
Centellas Casado et al.

(10) Patent No.: US 10,786,473 B2
(45) Date of Patent: *Sep. 29, 2020

(54) THERAPY FOR TRANSTHYRETIN-ASSOCIATED AMYLOIDOSIS

(71) Applicant: SOM INNOVATION BIOTECH, S.L., Barcelona (ES)

(72) Inventors: Marc Centellas Casado, Barcelona (ES); Raúl Insa Boronat, Barcelona (ES); Nuria Reig Bolaño, Barcelona (ES); Núria Gavaldà Batalla, Barcelona (ES)

(73) Assignee: SOM Innovation Biotech, S.L., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/569,055

(22) Filed: Sep. 12, 2019

(65) Prior Publication Data

US 2020/0138760 A1 May 7, 2020

Related U.S. Application Data

(63) Continuation of application No. 16/101,882, filed on Aug. 13, 2018, now Pat. No. 10,449,169, which is a continuation of application No. 15/448,054, filed on Mar. 2, 2017, now Pat. No. 10,045,956, which is a continuation of application No. 14/353,459, filed as application No. PCT/EP2012/070945 on Oct. 23, 2012, now Pat. No. 9,610,270.

(30) Foreign Application Priority Data

Oct. 24, 2011 (EP) .................................. 11382326

(51) Int. Cl.

| | |
|---|---|
| A61K 31/165 | (2006.01) |
| A61K 31/12 | (2006.01) |
| A61K 31/198 | (2006.01) |
| A61K 45/06 | (2006.01) |
| A61K 31/353 | (2006.01) |
| A61K 31/603 | (2006.01) |
| A61K 31/423 | (2006.01) |
| A61K 31/192 | (2006.01) |

(52) U.S. Cl.
CPC ............ *A61K 31/198* (2013.01); *A61K 31/12* (2013.01); *A61K 31/192* (2013.01); *A61K 31/353* (2013.01); *A61K 31/423* (2013.01); *A61K 31/603* (2013.01); *A61K 45/06* (2013.01)

(58) Field of Classification Search
CPC .... A61K 31/165; A61K 9/1635; A61K 31/12; C07D 263/58; C07D 263/20
USPC ................................ 514/375, 376, 620, 676
See application file for complete search history.

(56) References Cited

U.S. PATENT DOCUMENTS

| | | | |
|---|---|---|---|
| 9,610,270 B2 * | 4/2017 | Centellas Casado | .. A61K 31/12 |
| 10,045,956 B2 * | 8/2018 | Centellas Casado | .. A61K 31/12 |
| 10,449,169 B2 * | 10/2019 | Centellas Casado | .. A61K 31/12 |

* cited by examiner

*Primary Examiner* — Raymond J Henley, III
(74) *Attorney, Agent, or Firm* — King & Spalding

(57) ABSTRACT

It is provided a catechol-O-methyltransferase (COMT) inhibitor for use in the prevention and/or treatment of trans-thyretin-associated amyloidosis. It is also provided a catechol-O-methyltransferase (COMT) inhibitor for use in the prevention and/or treatment of transthyretin-associated amyloidosis in combination therapy with another COMT inhibitor, a benzoxazole derivative, iododiflunisal, diflunisal, resveratrol, tauroursodeoxycholic acid, doxocycline, or epigallocatechin-3-gallate.

16 Claims, 2 Drawing Sheets

THERAPY FOR TRANSTHYRETIN-ASSOCIATED AMYLOIDOSIS

CROSS REFERENCE TO RELATED APPLICATIONS

This application is a continuation of U.S. patent application Ser. No. 16/101,822, filed Aug. 13, 2018 (now U.S. Pat. No. 10,449,169), which is a continuation of U.S. patent application Ser. No. 15/448,054, filed Mar. 2, 2017 (now U.S. Pat. No. 10,045,956), which is a continuation of U.S. patent application Ser. No. 14/353,459, filed Apr. 22, 2014 (now U.S. Pat. No. 9,610,270), which is a national phase application under 35 U.S.C. § 371 of International Application No. PCT/EP2012/070945, filed Oct. 23, 2012, the disclosures of which are fully incorporated herein by reference.

The present invention is associated to the field of amyloid diseases and, particularly, to new compounds for the prevention and/or treatment of transthyretin-associated amyloidosis.

BACKGROUND ART

Amyloidosis refers to a variety of conditions in which amyloid proteins are abnormally deposited in organs and/or tissues. These amyloid proteins sometimes exist in an abnormal fibre-like form, called amyloid fibrils or amyloid deposits, that build up and progressively interfere with the structure and function of affected organs throughout the body. Different proteins are implicated in different types of amyloid disease, and treatment depends on the particular amyloid protein.

Transthyretin-associated amyloidosis is a general denomination for a group of amyloid diseases that are specifically associated to transthyretin abnormal misfolding, aggregation (fibril formation) and subsequent deposition. Transthyretin (TTR) protein is a serum and cerebrospinal fluid carrier of the thyroid hormone thyroxine and retinol. Mutations in the TTR gene, which is located on human chromosome 18q12.1-11.2, sometimes result in a desestabilization of the TTR protein, leading to abnormal aggregation and transthyretin-associated amyloid disease. More than 80 amyloid forming variants of TTR are known, of which the most frequent is called TTR V30M.

Familial amyloid polyneuropathy (FAP), also called transthyretin-associated hereditary amyloidosis, transthyretin amyloidosis or Corino de Andrade's disease, is an autosomal dominant neurodegenerative disease. Usually manifesting itself between 20 and 40 years of age, it is characterized by pain, paresthesia, muscular weakness and autonomic dysfunction. In its terminal state, the kidneys and the heart are affected. FAP is characterized by the systemic deposition of amyloid variants of the TTR protein, especially in the peripheral nervous system, causing a progressive sensory and motorial polyneuropathy. This disease is by far the most common type of hereditary amyloidosis in the world.

Other types of transthyretin-associated amyloidosis are familial amyloid cardiomyopathy and senile systemic amyloidosis, caused by the deposition of amyloid TTR in the heart, and leptomeningeal amyloidosis, where amyloid deposits of TTR are found in the walls of leptomeningeal vessels, in pia-arachnoid, and also in subpial space deposits. The latter condition is associated with a clinical picture of central nervous system impairment manifest as dementia, ataxia, and spasticity.

Whilst there is, as yet, no treatment that blocks amyloid deposition or speeds up its removal, treatment of amyloid diseases is aimed at supporting the function of failing organs. Liver transplantation has been often used as a treatment for transthyretin-associated amyloidosis, particularly FAP, since TTR protein is mainly produced in the liver. Replacement of the liver containing a mutant TTR gene by a liver that makes normal transthyretin protein is aimed at preventing the formation of further amyloid and can stabilise the disease. Liver transplantation has been performed in patients with FAP, with great success in many cases. However, a liver transplantation is not always an available option and, besides, as experience increases, it is becoming clear that liver transplantation for FAP should take place before too much damage to the nerves or heart has already occurred. Sadly, the latter may occur without causing any symptoms.

Very few compounds have been described as exerting an inhibitory activity against fibril formation and subsequent deposition of TTR. Among these, iododiflunisal has been reported as a potent amyloid inhibitor in vitro by Gales et al (Gales L, Macedo-Ribeiro S, Arsequell G, Valencia G, Saraiva M J, Damas A M. "Human transthyretin in complex with iododiflunisal: structural features associated with a potent amyloid inhibitor". *Biochem J*, 2005, vol. 388, p. 615-621). Further, patent application WO 2005/113523 discloses benzoxazole compounds for stabilizing TTR amyloid protein, thus preventing the formation of TTR amyloid fibrils. These compounds are claimed as useful for the treatment of transthyretin-associated amyloid diseases.

Particularly, a benzoxazole derivative called tafamidis (2-(3,5-dichlorophenyl)-1,3-benzoxazole-6-carboxylic acid has been described to inhibit TTR abnormal aggregation and fibril formation, and is undergoing clinical trials for the treatment of FAP. Despite being a promising perspective, tafamidis is still under evaluation in the main official medicine registration offices. Thus, the clinical relevance of tafamidis still needs to be clarified.

Despite the considerable effort that has been made in the field, there is to date no effective pharmacological therapy for the treatment of FAP. It is therefore desirable to provide alternative compounds for the treatment of FAP and other transthyretin-associated amyloidosis.

SUMMARY OF THE INVENTION

The inventors have surprisingly found that catechol-O-methyltransferase (COMT) inhibitors are useful for the prevention and/or treatment of TTR-associated amyloidosis.

As shown in the examples below, the COMT inhibitor tolcapone has a high inhibiting activity against TTR amyloid formation. The good inhibitory activity of tolcapone is revealed by its low $IC_{50}$ and high percent amyloidosis reduction (RA %) values.

Thus, a first aspect of the present invention relates to a COMT inhibitor for use in the prevention and/or treatment of TTR-associated amyloidosis. This aspect can be reformulated as use of a COMT inhibitor for the preparation of a medicament for the prevention and/or treatment of a TTR-associated amyloidosis.

It also forms part of the invention a method for the prevention and/or treatment of a TTR-associated amyloidosis comprising administering a COMT inhibitor to a subject in need thereof. In a particular embodiment, the subject in need of the prevention and/or treatment is a mammal, including a human. In a further preferred embodiment, the mammal is a human.

As compared to tafamidis, which is so far the most advanced pharmacological compound for FAP treatment, tolcapone has a four fold lower IC$_{50}$ in vitro, which means that the concentration of tolcapone needed to inhibit 50% of TTR fibril formation is much lower than that of tafamidis (see examples below). The examples below additionally demonstrate that tolcapone binds to TTR and prevents TTR-induced cytotoxicity to a greater extent than tafamidis.

According to these results, tolcapone is more effective in reducing TTR fibril formation than the reference tafamidis compound. In addition to preventing TTR fibril formation, the inventors have found that tolcapone exhibits an important disruption activity over existing TTR fibrils. The results presented below demonstrate that tolcapone's TTR fibril disruption activity is higher than that of tafamidi's.

COMT inhibitors are well known in the state of the art as compounds that inhibit the action of catechol-O-methyl transferase, an enzyme that is involved in degrading neurotransmitters (Mannisto and Kaakkola, *Pharm. Rev.*, 1999, vol 51, p. 593-628). COMT inhibitor activity can be determined by methods known in the art, for instance the method disclosed in Zürcher et al (*Biomedical Chromatography*, 1996, vol. 10, p. 32-36). COMT inhibitors are well known in the art of pharmacology for the treatment of Parkinson's disease in conjunction with dopaminergic agents such as L-DOPA.

Several COMT inhibitors have been described. Tolcapone, entacapone, and nitecapone belong to the so called "second generation COMT inhibitors", which have been shown to be potent, highly selective, and orally active COMT inhibitors. Nitrocatechol is the key structure in these molecules (*Pharm. Rev.*, 1999, vol 51, p. 593-628, supra). Thus, in one embodiment the COMT inhibitor for use in the prevention and/or treatment of TTR-associated amyloidosis is a nitrocatechol compound. In a particular embodiment, the nitrocatecol compound has the following formula I

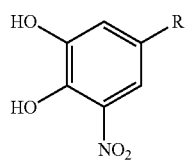

(Formula I)

or a pharmaceutically acceptable salt thereof, wherein R=—C(O)-PhCH$_3$, —CH=C(CN)—C(O)-NEt$_2$ or CH=C(C(O)CH$_3$)$_2$.

In another embodiment of the first aspect of the invention the COMT inhibitor is tolcapone, entacapone or nitecapone, or pharmaceutically acceptable salts thereof.

In a particular embodiment the COMT inhibitor is tolcapone, or a pharmaceutically acceptable salt thereof. Tolcapone (formula II) is a yellow, odorless, non-hygroscopic, crystalline compound with a relative molecular mass of 273.25. Its empirical formula is C$_{14}$H$_{11}$NO$_5$. The chemical name of tolcapone is 3,4-dihydroxy-4'-methyl-5-nitrobenzophenone and its CAS reference number is 134308-13-7.

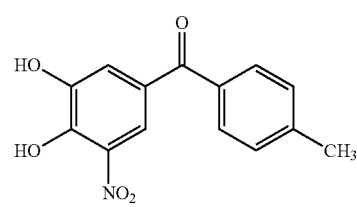

(Formula II)

In another embodiment of the first aspect of the invention the COMT inhibitor is entacapone, or a pharmaceutically acceptable salt thereof. Entacapone (formula III) is a yellow crystalline compound with molecular mass of 305.29. Its empirical formula is C$_{14}$H$_{15}$N$_3$O$_5$. The chemical name of entacapone is (2E)-2-cyano-3-(3,4-dihydroxy-5-nitrophenyl)-N,N-diethyl-2-propenamide and its CAS reference number is 130929-57-6.

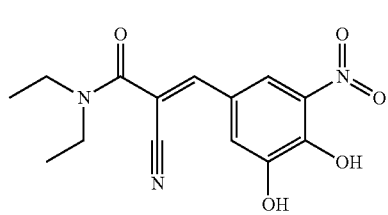

(Formula III)

Since these compounds are drugs that have been approved for medical use in the treatment of Parkinson Disease by the Food and Drug Administration (FDA) and European Medicines Agency (EMA) since 1998, the bioavailability and safety profile of tolcapone and entacapone have been studied in several clinical trials. As such, these compounds have an acceptable safety profile for human use and good bioavailability. Their safety profile in conjuction with their high inhibitory activity against TTR fibril formation render the COMT inhibitors highly promising drugs for the prevention and/or treatment of TTR-associated amyloidosis.

Additionally, since these compounds have already been subjected to clinical trials for the treatment of human disease, the clinical poof-of-concept is less risky (and faster) to achieve when compared with classical development of new chemical entities. In this sense, it is important to highlight that considerable fewer experimentation needs to be done in human beings and animals, subsequently implying lower developmental costs and, more importanly, less sufferings to humans and animals.

In another embodiment of the first aspect of the invention the COMT inhibitor is nitecapone, or a pharmaceutically acceptable salt thereof. Nitecapone (formula IV) is a compound with molecular mass of 265.21. Its empirical formula is C$_{12}$H$_{11}$NO$_6$, the chemical name 3-[(3,4-Dihydroxy-5-nitrophenyl)methylene]-2,4-pentanedione, and CAS reference number 116313-94-1.

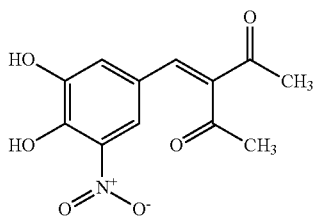

(Formula IV)

In a preferred embodiment of the invention the TTR-associated amyloidosis is FAP. In another embodiment the TTR-associated amyloidosis is senile systemic amyloidosis. In another embodiment the TTR-associated amyloidosis is familial amyloid cardiomyopathy. In yet another embodiment the TTR-associated amyloidosis is leptomeningeal amyloidosis.

COMT inhibitors, such as those defined above can be used either alone or in combination with other therapeutic agents for the prevention and/or treatment of TTR-associated amyloidosis. Thus, in a second aspect, the invention refers to a combination of a COMT inhibitor and an additional therapeutic agent for the prevention and/or treatment of a TTR-associated amyloidosis. This embodiment can be reformulated as a combination of a COMT inhibitor and an additional therapeutic agent for the prevention and/or treatment of a TTR-associated amyloidosis. Further, it also forms part of the invention a method for the prevention and/or treatment of a transthyretin-associated amyloidosis which comprises administering to a subject in need thereof a combination of a COMT inhibitor and an additional therapeutic agent. Non-limiting examples of additional therapeutic agents for use in the second aspect of the invention are another COMT inhibitor, a benzoxazole derivative, iododiflunisal, diflunisal, resveratrol, tauroursodeoxycholic acid, doxocycline and epigallocatechin-3-gallate (EGCG). Preferably, the COMT inhibitor is a nitrocatechol compound of formula I or a pharmaceutically acceptable salt thereof as defined for the first aspect of the invention. The skilled person will understand that pharmaceutically acceptable salts of the above mentioned additional therapeutic agents can also be used in the combination of the second aspect of the invention.

In one embodiment of the second aspect of the invention it is provided a combination of a COMT inhibitor and an additional therapeutic agent selected from the group consisting of another COMT inhibitor, a benzoxazole derivative, and iododiflunisal for use in the prevention and/or treatment of transthyretin-associated amyloidosis. Preferably, the COMT inhibitor is a nitrocatechol compound of formula I or a pharmaceutically acceptable salt thereof as defined for the first aspect of the invention.

Benzoxazole derivatives are disclosed in the international patent application WO2005113523 as compounds that stabilize the native state of TTR, thereby inhibiting protein misfolding. In one embodiment of the second aspect of the invention, the benzoxazole derivatives are compounds of formula V:

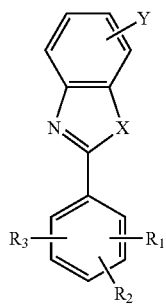

(Formula V)

or a pharmaceutically acceptable salt thereof, wherein:
Y is COOR, tetrazolyl, CONHOR, B(OH)$_2$ or OR;
X is O; and
$R^1$, $R^2$ and $R^3$ are each independently selected from hydrogen, halo, OR, B(OH)$_2$ or CF$_3$, and
wherein R is hydrogen, $C_1$-$C_6$ alkyl, $C_1$-$C_6$ alkenyl, $C_1$-$C_6$ alkynyl, $C_1$-$C_6$ cycloalkyl, $C_1$-$C_6$ heterocyclyl, phenyl, xylyl, naphthyl, thienyl, indolyl or pyridyl.

In a particular embodiment of the second aspect of the invention the COMT inhibitor is a nitrocatechol compound of formula I or a pharmaceutically acceptable salt thereof as defined for the first aspect of the invention and the additional therapeutic agent is a benzoxazole derivative of formula V or a pharmaceutically acceptable salt thereof as defined above.

In another embodiment of the second aspect of the invention the benzoxazole derivative is a compound of formula VI

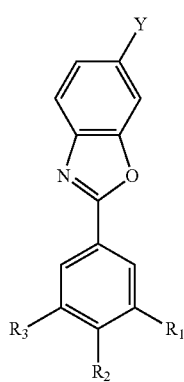

(Formula VI)

or a pharmaceutically acceptable salt thereof, wherein:
Y is COOH, or OH; and
$R^1$, $R^2$ and $R^3$ are each independently selected from hydrogen, halo, OH, B(OH)$_2$ or CF$_3$.

In a particular embodiment the COMT inhibitor is a nitrocatechol compound of formula I or a pharmaceutically acceptable salt thereof as defined for the first aspect of the invention and the additional therapeutic agent is a benzoxazole derivative of formula VI or a pharmaceutically acceptable salt thereof as defined above.

In another embodiment the benzoxazole derivative is tafamidis. In a particular embodiment the COMT inhibitor is a nitrocatechol compound of formula I or a pharmaceutically acceptable salt thereof as defined for the first aspect of the invention and the additional therapeutic agent is tafamidis. In another particular embodiment the COMT inhibitor is tolcapone or a pharmaceutically acceptable salt thereof and the additional therapeutic agent is tafamidis.

In another embodiment of the second aspect of the invention, the additional therapeutic agent is iododiflunisal. In a particular embodiment the COMT inhibitor is a nitrocatechol compound of formula I or a pharmaceutically acceptable salt thereof as defined for the first aspect of the invention and the additional therapeutic agent is iododiflunisal. In another particular embodiment the COMT inhibitor is tolcapone or a pharmaceutically acceptable salt thereof and the additional therapeutic agent is iododiflunisal.

In another particular embodiment, the COMT inhibitor is combined with another COMT inhibitor. Preferably, the COMT inhibitors are nitrocatechol compounds of formula I or pharmaceutically acceptable salts thereof as defined for the first aspect of the invention. For instance, the invention provides a combination of tolcapone and entacapone for the prevention and/or treatment of a TTR-associated amyloidosis.

In a further embodiment of the second aspect of the invention it is provided a combination of a COMT inhibitor and an additional therapeutic agent selected from the group consisting of diflunisal, resveratrol, tauroursodeoxycholic acid, doxocycline and EGCG for use in the prevention and/or treatment of a TTR-associated amyloidosis. EGCG is a the main and most significant polyphenol in green tea. In the sense of the present invention, EGCG can be used as an isolated compound or forming part of a plant extract, particularly a tea extract. Preferably, the COMT inhibitor is a nitrocatechol compound of formula I or a pharmaceutically acceptable salt thereof as defined for the first aspect of the invention. More preferably the COMT inhibitor is tolcapone or a pharmaceutically acceptable salt thereof. A particular embodiment provides a combination of tolcapone or a pharmaceutically acceptable salt thereof and EGCG for use in the prevention and/or treatment of a TTR-associated amyloidosis.

As will be apparent to the skilled in the art, the combination of the present invention is effective not only when the active ingredients are used in a single composition, but also when used in two different compositions, either administered simultaneously, sequentially or separately after a certain period of time. Furthermore, the skilled in the art will understand that the COMT inhibitor can be prescribed to be used together with the other active ingredient in a combination therapy in order to prevent and/or treat a transthyretin-associated amyloidosis, and viceversa.

Thus, a third aspect of the present invention provides a COMT inhibitor for use in the prevention and/or treatment of transthyretin-associated amyloidosis in combination therapy with an additional therapeutic agent. This embodiment may be reformulated as use of a COMT inhibitor for the preparation of a medicament for the prevention and/or treatment of transthyretin-associated amyloidosis in combination therapy with an additional therapeutic agent. It also forms part of the invention a method for the prevention and/or treatment of a transthyretin-associated amyloidosis which comprises administering to a subject in need thereof a COMT inhibitor in combination with an additional therapeutic agent.

Non-limiting examples of additional therapeutic agents for use in the third aspect of the invention are another COMT inhibitor, a benzoxazole derivative, iododiflunisal, diflunisal, resveratrol, tauroursodeoxycholic acid, doxocycline and EGCG. Preferably, the COMT inhibitor is a nitrocatechol compound of formula I or a pharmaceutically acceptable salt thereof as defined for the first aspect of the invention. The skilled person will understand that pharmaceutically acceptable salts of the above mentioned additional therapeutic agents can also be used in the combination therapy of the third aspect of the invention.

In one embodiment of the third aspect of the invention it is provided a COMT inhibitor for use in the prevention and/or treatment of transthyretin-associated amyloidosis in combination therapy with an additional therapeutic agent selected from the group consisting of another COMT inhibitor, a benzoxazole derivative, and iododiflunisal. Preferably, the COMT inhibitor is a nitrocatechol compound of formula I or a pharmaceutically acceptable salt thereof as defined for the first aspect of the invention.

In a particular embodiment of the third aspect of the invention, the additional therapeutic agent is another COMT inhibitor. Preferably, the COMT inhibitors are nitrocatechol compounds of formula I or pharmaceutically acceptable salts thereof as defined for the first aspect of the invention. For example, the invention provides tolcapone for the prevention and/or treatment of a TTR-associated amyloidosis in combination with entacapone. In another particular embodiment, the additional therapeutic agent is a benzoxazole derivative.

Preferably, said benzoxazole derivative is a compound of formula V or VI or pharmaceutical salts thereof as defined for the second aspect of the invention. For example, the invention provides a COMT inhibitor for the prevention and/or treatment of a TTR-associated amyloidosis in combination with tafamidis. Preferably, the COMT inhibitor is a nitrocatechol compound of formula I or a pharmaceutically acceptable salt thereof as defined for the first aspect of the invention. More preferably the COMT inhibitor is tolcapone or a pharmaceutically acceptable salt thereof. Thus the invention provides tolcapone for the prevention and/or treatment of a TTR-associated amyloidosis in combination with tafamidis. In yet another embodiment, the additional therapeutic agent is iododiflunisal. In yet another embodiment, the additional therapeutic agent is iododiflunisal and the COMT inhibitor is a nitrocatechol compound of formula I or a pharmaceutically acceptable salt thereof as defined for the first aspect of the invention. The invention thus provides tolcapone or a pharmaceutically acceptable salt thereof for the prevention and/or treatment of a TTR-associated amyloidosis in combination with iododiflunisal.

In a further embodiment of the third aspect of the invention it is provided a COMT inhibitor for use in the prevention and/or treatment of transthyretin-associated amyloidosis in combination therapy with an additional therapeutic agent selected from the group consisting of diflunisal, resveratrol, tauroursodeoxycholic acid, doxocycline and EGCG for use in the prevention and/or treatment of a TTR-associated amyloidosis. Preferably, the COMT inhibitor is a nitrocatechol compound of formula I or a pharmaceutically acceptable salt thereof as defined for the first aspect of the invention. More preferably the COMT inhibitor is tolcapone or a pharmaceutically acceptable salt thereof. In a particular embodiment the invention provides tolcapone or a pharmaceutically acceptable salt thereof for use in the prevention and/or treatment of transthyretin-associated amyloidosis in combination therapy with EGCG.

A fourth aspect of the invention provides a therapeutic agent selected from the group consisting of a benzoxazole derivative, iododiflunisal, diflunisal, resveratrol, tauroursodeoxycholic acid, doxocycline and EGCG, for use in the prevention and/or treatment of transthyretin-associated amyloidosis in combination therapy with a COMT inhibitor. Preferably, the COMT inhibitor is a nitrocatechol compound of formula I or a pharmaceutically acceptable salt thereof as defined for the first aspect of the invention. The skilled person will understand that pharmaceutically acceptable salts of the above mentioned therapeutic agents can also be used in the combination therapy of the fourth aspect of the invention.

In one embodiment of the fourth aspect of the invention it is provided a therapeutic agent selected from the group consisting of a benzoxazole derivative and iododiflunisal for use in the prevention and/or treatment of transthyretin-associated amyloidosis in combination therapy with a COMT inhibitor. Preferably, the COMT inhibitor is a nitrocatechol compound of formula I or a pharmaceutically acceptable salt thereof as defined for the first aspect of the invention.

In a particular embodiment of the fourth aspect of the invention, the therapeutic agent is a benzoxazole derivative. Preferably, said benzoxazole derivative is a compound of formula V or VI or pharmaceutical salts thereof as defined for the second aspect of the invention. For example, the invention provides tafamidis for the prevention and/or treatment of TTR-associated amyloidosis in combination with a COMT inhibitor. Preferably, the COMT inhibitor is a nitrocatechol compound of formula I or a pharmaceutically acceptable salt thereof as defined for the first aspect of the invention. More preferably the COMT inhibitor is tolcapone or a pharmaceutically acceptable salt thereof. Thus the invention provides tafamidis for the prevention and/or treatment of a TTR-associated amyloidosis in combination with tolcapone or a pharmaceutically acceptable salt thereof. In yet another embodiment, the therapeutic agent is iododiflunisal. In yet another embodiment, the additional therapeutic agent is iododiflunisal and the COMT inhibitor is a nitrocatechol compound of formula I or a pharmaceutically acceptable salt thereof as defined for the first aspect of the invention. The invention provides iododiflunisal for the prevention and/or treatment of a TTR-associated amyloidosis in combination with tolcapone or a pharmaceutically acceptable salt thereof.

In a further embodiment of the fourth aspect of the invention it is provided a therapeutic agent selected from the group consisting of diflunisal, resveratrol, tauroursodeoxycholic acid, doxocycline and EGCG for use in the prevention and/or treatment of transthyretin-associated amyloidosis in combination therapy with a COMT inhibitor. Preferably, the COMT inhibitor is a nitrocatechol compound of formula I or a pharmaceutically acceptable salt thereof as defined for the first aspect of the invention. More preferably, the COMT inhibitor is tolcapone or a pharmaceutically acceptable salt thereof. A particular embodiment provides EGCG for use in the prevention and/or treatment of a TTR-associated amyloidosis in combination therapy with tolcapone or a pharmaceutically acceptable salt thereof.

Additionally, the COMT inhibitor can be used as adjuvant treatment before and/or after liver transplant in a patient with a TTR-associated amyloidosis. Preferably, said COMT inhibitor is a nitrocatechol compound of formula I or a pharmaceutically acceptable salt thereof as defined for the first aspect of the invention.

The invention also provides a pharmaceutical composition comprising a therapeutically effective amount of a COMT inhibitor together with pharmaceutically acceptable excipients and/or carriers for the prevention and/or treatment of a TTR-associated amyloidosis. Preferably, said COMT inhibitor is a nitrocatechol compound of formula I or a pharmaceutically acceptable salt thereof as defined for the first aspect of the invention.

The expression "therapeutically effective amount", also referred as "dose", refers to the amount of a compound that, when administered, is sufficient to prevent development of, or alleviate to some extent, one or more of the symptoms of the disease which is addressed. The particular dose of compound administered according to this invention will be determined by the particular circumstances surrounding the case, including the compound administered, the route of administration, the particular condition being treated, and similar considerations.

The expression "pharmaceutically acceptable excipients and/or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

Any pharmaceutically acceptable salt of the COMT inhibitor can be used for the purposes of the invention. The term "pharmaceutically acceptable salt" refers to salts prepared from pharmaceutically acceptable non-toxic bases. Preferably, the salt is an alkaline or alkaline earth metal salt.

In one embodiment of the invention, the COMT inhibitor is administered to a patient in oral unit dosage form. Dosage forms include solid dosage forms like tablets, powders, capsules, sachets, as well as liquid syrups, suspensions and elixirs. COMT inhibitors and excipients can be formulated into compositions and dosage forms according to methods known in the art. In a particular embodiment, the COMT inhibitor is administered as a tablet, a pill or a capsule. However, COMT inhibitors can also be administrered to a patient as an ingredient of injection dosage forms. Injection dosage forms can include liquids for intradermal, intravenous, intramuscular or subcutaneous injection, solutions for perfusion, powder for reconstitution of liquid injections, and pre-filled syringes. In the sense of the present invention it may also be adequate to formulate the COMT inhibitor for intranasal or inhaled administration, or for topic administration in the form of, for instance, a cream, a gel, an ointment or a dermal patch. Methods for the preparation of these formulations are known in the art. Further, the COMT inhibitor can be formulated as a controlled release dosage form. Controlled release dosage forms are known in the art and particularly desirable for the treatment of chronic diseases or for the administration of active agents that can be toxic at high doses or that show a low half-life pattern when administered to the patient. Preferably, the COMT inhibitor is a nitrocatechol compound of formula I or a pharmaceutically acceptable salt thereof as defined for the first aspect of the invention.

As mentioned above, a therapeutically effective amount (or dose) of COMT inhibitor in the sense of the present invention is the amount of said compound that is sufficient to prevent or alleviate to some extent one or more of the symptons of a TTR-associated amyloidosis. For instance, an effective daily dose of tolcapone for human use could range between 20 and 600 mg and an effective daily dose of entacapone for human use could range between 1600 and 2000 mg.

Thus, the dose of COMT inhibitor to be administered can be between 0.1 and 16000 mg/day, or between 0.1 and 12000 mg/day, or between 0.1 and 10000 mg/day, or between 0.1 and 5000 mg/day, or between 0.1 and 3000 mg/day. In a particular embodiment, the dose of COMT inhibitor to be administered is between 1 and 3000 mg/day. In another embodiment, the dose is between 1 and 2000 mg/day. Preferably, the COMT inhibitor is a nitrocatechol compound of formula I or a pharmaceutically acceptable salt thereof as defined for the first aspect of the invention.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1: Kinetic Turbidity Assay

Materials

Figure 1:
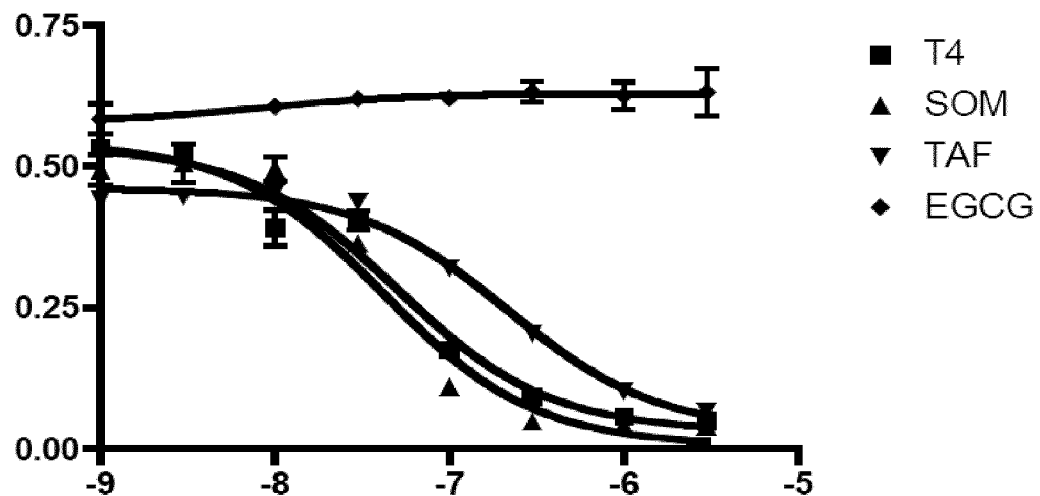
FIG. 1. Assay of competition with T4 for the binding to TTR wild type (WT) by gel filtration: Curves of T4 displacement from TTR WT by different compounds. Y axis: Amount of TTR-bound T4/total T4; X-axis: log 10 concentration of compound (molar units). Values correspond to a representative experiment done in duplicates, represented as average+/−standard deviation. Test compounds: Thyroxine (T4), Tolcapone (SOM), Tafamidis (TAF), and (−)-epigallocatechin-3-gallate (EGCG).

Recombinant Y78F TTR protein, which is a Tyr78Phe highly amyloidogenic variation of human TTR, was produced as reported in Dolado et al (Dolado I, Nieto J, Saraiva M J, Arsequell G, Valencia G, Planas A. "Kinetic Assay for High-Throughput Screening of In Vitro Transthyretin Amyloid Fibrillogenesis Inhibitors". *J. Comb. Chem.*, 2005, vol. 7, p. 246-252).

Tolcapone was obtained from Santa Cruz Biotechnology, Inc. Iododiflunisal, was prepared from diflusinal (Sigma) by reaction with bis(pyridine)iodonium tetrafluoroborate ($IPy_2BF_4$) as described by Barluenga et al (Barluenga J, González J M, García-Martín M A, Campos P J, Asensio G. "An expeditious and general aromatic iodination procedure. *J Chem Soc Chem Commun*, 1992, vol. 14, p. 1016-1017). Tafamidis can be prepared by the methods disclosed in the international patent application WO2005113523. Stocks of compounds assayed as inhibitors were dissolved in DMSO (spectrophotometry grade from Sigma) at 1.5 mM concentration. Working solutions were prepared by diluting the stock solution 1:4 in H2O/DMSO (2:1). In all cases, DMSO concentration was adjusted to 5% (v/v) in the final reaction assay mixture.

Methods

The assay was performed according to the procedure described in Dolado et al (supra). The assay comprises two stages, one stage where the Y78F protein is incubated together with the inhibitor during 30 minutes, and a second stage where fibril formation is induced by a change in pH and absorbance is measured along 1.5 h. Briefly, the assay was performed as follows:

First, the following solutions were prepared: Protein Y78F stock: 4 mg/mL in 20 mM phosphate, 100 mM KCl, pH 7.6. Incubation buffer: 10 mM phosphate, 100 mM KCl, 1 mM EDTA, pH 7.6. Dilution buffer: 400 mM sodium acetate, 100 mM KCl, 1 mM EDTA, pH 4.2.

For each inhibitor the following protocol was followed: Exact protein concentration of the stock solution was determined by $Abs_{280}$ and according to this value, the volume of Y78F stock to be added to have a final protein well concentration of 0.4 mg/mL was calculated and dispensed into 6 wells of a 96-well microplate. Different volumes of working inhibitor solution were added to give final concentrations ranging from 0 to 40 µM, and the final DMSO content of each well was adjusted to 5% by adding the corresponding volume of a H₂O/DMSO (1:1) solution. Incubation buffer was then added up to a volume of 100 µL. The plate was incubated at 37° C. in a thermostated microplate reader with orbital shaking 15 s every minute for 30 min. A 100 µL portion of dilution buffer was dispensed to each well, and the mixture was incubated at 37° C. with shaking (15 s every min) in the microplate reader. Absorbance at 340 nm was monitored for 1.5 h at 1 min intervals. Data were collected and analyzed using Microsoft Excel software. All assays were done in duplicate.

Result Analysis

After following the general procedure indicated above, time-course curves were obtained, from which the initial rates of fibril formation ($V_0$) were calculated as the slopes of the linear increase of absorbance. When plotting the initial rates vs inhibition concentration, an exponential decay was obtained with all inhibitors analyzed. Data were fitted to equation (1):

$$V_0 = A + B * e^{-C[I]} \qquad (1),$$

where $V_0$ is the initial rate of fibril formation (in absorbance units per hour, $Abs*h^{-1}$), and [I] is the concentration of the inhibitor (µM). Adjustable parameters are A ($Abs*h^{-1}$), residual aggregation rate at high concentration of inhibitor; B ($Abs*h^{-1}$), amplitude or maximum decrease of initial rate of fibril formation; and C ($µM^{-1}$), the exponential constant.

A+B is equal to the initial rate of fibril formation under the assay conditions in the absence of inhibitor.

The following parameters were estimated to evaluate the potency of a compound as fibril formation inhibitor: $IC_{50}$: concentration of inhibitor at which the initial rate of fibril formation is one-half that without inhibitor. RA (%)=100*B/(A+B): percent reduction of fibril formation rate at high inhibitor concentration relative to the rate at [I]=0. Results of evaluation of the inhibition properties of assayed compounds are summarized in Table 1.

TABLE 1

$IC_{50}$ and percentage of amyloidosis reduction (RA) values for TTR fibril formation inhibitors

| Compound | $IC_{50}$ (μM) | RA (%) |
|---|---|---|
| Tolcapone | 4.8 | 85.8 |
| Iododiflunisal | 3.9 | 99.8 |
| Tafamidis | 16.9 | 99 |

It can be observed by the above results that tolcapone is an effective inhibitor of TTR fibril formation, as it showed a low $IC_{50}$ and a high RA. According to their $IC_{50}$ values, tolcapone has a similar inhibition capacity as compared with iododiflunisal, which has been reported as one of the most potent TTR fibril formation inhibitors in vitro. Further, according to the $IC_{50}$, tolcapone is more effective than tafamidis, since it shows an $IC_{50}$ which is four times lower than tafamidis. These results demonstrate that tolcapone is a promising drug for TTR-related amyloidosis, such as FAP, familial amyloid cardiomyopathy senile systemic amyloidosis and leptomeningeal amyloidosis.

Example 2: End-Point Turbidity Assay with a Familiar Amyloid Cardiomyopathy Mutant Variant of TTR Materials Recombinant V122I TTR protein, which is an amyloidogenic variation of human TTR associated with Familial Amyloid Cardiomyopathy (FAC), was produced by following the same procedure described for the Y78F variant used in Example 1. Plasmid DNA expressing the V122I mutant was prepared by site-directed mutagenesis as reported for Y78F in Dolado et al (supra). but using the following primers: 5'-GGATTGGTGATGACAGCCGT-3' and 5'-ACGGCTGTCATCACCAATCC-3'. Tolcapone and Iododiflunisal were obtained as described in Example 1.

Methods

This assay is used for TTR variants with lower amyloidegenicity than the Y78F variant when the kinetic turbidity assay is not sensitive enough for accurate measurements. The procedure followed to test the inhibitors by this end-point assay at 72 h is reported in Dolado et al, (supra). V122I TTR was incubated with the inhibitor under the same conditions described above for the kinetic turbidity assay (Example 1), using V122I protein at a concentration of 0.4 mg/mL and three different concentrations of inhibitor: 3.6, 7.2 and 21.8 microM, corresponding to 0.5×[protein], 1×[protein], and 3×[protein]. After acid induction (addition of dilution buffer), samples were incubated without shaking for 72 h at 37° C. and then homogenized by mixing to resuspend any fibrils present. Turbidity was measured at 340 nm and normalized to amyloidogenesis in the absence of inhibitor.

Result

The inhibitory potency of the tested compounds was evaluated as the percentage of absorvance reduction of the inhibitor-containing samples when compared with the inhibitor-free control sample.

TABLE 2

% Fibril Reduction values for V122I TTR fibril formation inhibitors

| Inhibitor concentration: | 0.5×[protein] | 1×[protein] | 3×[protein] |
|---|---|---|---|
| Tolcapone | 79.3% | 84.3% | 100.0% |
| Iododiflunisal | 83.2% | 85.0% | 88.2% |

% Fibril reduction=100×(1−turbidity sample/turbidity blank), where turbidity sample is the turbidity measured in the presence of inhibitor, and turbidity blank is that in the absence of inhibitor.

The above results show that tolcapone effectively inhibits fibril formation by V122I mutant ATTR, even at a inhibitor:protein molar ratio of 1:2 (0.5×[protein]). According to these values, tolcapone has a similar inhibition capacity as compared with iododiflunisal. These results demonstrate that tolcapone is a promising drug for TTR-related amyloidosis, including familial amyloid cardiomyopathy, which is caused mainly by the V122I mutation.

Examples 3-6

Materials for Examples 3-6

Tolcapone and tafamidis were obtained as described in example 1. The Epigallocatechin-3-gallate (EGCG, CAS No. 989-51-5) was purchased from Cayman Chemicals (#70935). Recombinant wild-type TTR (TTR WT), TTR Y78F and TTR L55P variants were produced in a bacterial expression system using *Escherichia coli* BL21. Recombinant TTRs were isolated and purified as previously described (Ferreira et al, 2009, *FEBS Lett*, vol. 583, p. 3569-76). Whole blood from TTR V30M heterozygote carriers and from control individuals were obtained from a collection of samples available at the Molecular Neurobiology Group, IBMC (University of Porto). Blood samples had been collected in the presence of EDTA and centrifuged for the separation of plasma. Plasmas had been kept frozen at −20° C.

Example 3: Assay of Competition with Thyroxine (T4) for the Binding to TTR Wild Type (WT) by Gel Filtration Binding of small molecule ligands to the T4 binding sites of TTR might stabilize the TTR tetramer and slow tetramer dissociation and amyloidogenesis in vitro. To asses binding, competition of test compounds with T4 (Sigma-Aldrich) for binding to TTR WT was assayed quantitatively by a gel filtration procedure, using a constant amount of TTR (100 μL of 60 nM solution) incubated with a trace amount of radiolabeled [125I]T4 (corresponding to 50.000 cpm; 125I-T4 specific activity 1250 μCi/μg from Perkin-Elmer, MA, USA) and with 100 μL of solution of either test compounds or T4 (positive control) at different concentrations, namely 0, 20, 60, 200, 600, 2000 6000 and 20000 nM (0-10 μM final concentration) (Ferreira et al, 2011, *FEBS Lett*., vol. 585, p. 2424-30). The negative control was prepared with the protein, plus labelled T4 plus 100 μL of THE (absence of competitor). All solutions were prepared in THE buffer (Tris 0.1 M, NaCl 0.1 M, EDTA 1 mM). All samples were prepared in duplicate. Radioactivity was measured in each sample, in a gamma scintillation counter Wizard 14701, Wallac. The samples were then incubated overnight at 4° C. After incubation, T4 bound to TTR was separated from unbound T4 by filtration through a P6DG gel filtration column (1 mL, BioRad). Radioactivity was measured in the eluted samples. The results were expressed as the amount of TTR-bound T4/total T4 against Log total concentration of test compounds (competitors). Data was fitted to a one-site binding competition non-linear regression curve with GraphPad Prism software using the following equation: Y=Bottom+(Top−Bottom)/(1+10^(X−Log EC50))

FIG. 1 shows the results for competition with T4 for the binding to TTR wild type of competitors: Thyroxine (T4), Tolcapone (SOM), Tafamidis (TAF), and (−)-epigallocatechin-3-gallate (EGCG). The results are shown as the curves of T4 displacement from TTR WT by the different compounds. From each dose-response curve, the $EC_{50}$ value (inhibitor concentration at which half of the bound T4 is displaced) for each compound is determined. Further, the relative potency for the inhibition of binding of T4, defined as the ratio $EC_{50}$ (T4)/EC50 (tested compound), was also calculated and is shown in table 3.

TABLE 3

$EC_{50}$ and relative potency of drug inhibition of T4 binding

|  | EC50 nM | Relative potency of drug inhibition of T4 binding |
| --- | --- | --- |
| Thyroxine (T4) | 50.11 nM | 1 |
| Tolcapone | 41.85 nM | 1.19 |
| Tafamidis | 214.4 nM | 0.23 |
| EGCG | — | No affinity |

These results demonstrate that tolcapone and tafamidis present similar binding affinity to TTR, while EGCG does not compete with T4 for the binding to TTR. The $EC_{50}$ of tolcapone was 4 times lower than that of tafamidis, which demonstrates that tolcapone is more effective in binding the TTR tetramer, suggesting a higher anti-amyloidogenic potential.

Example 4: Assessment of TTR Tetrameric Stability by Isoelectric Focusing (IEF)

Figure 2:
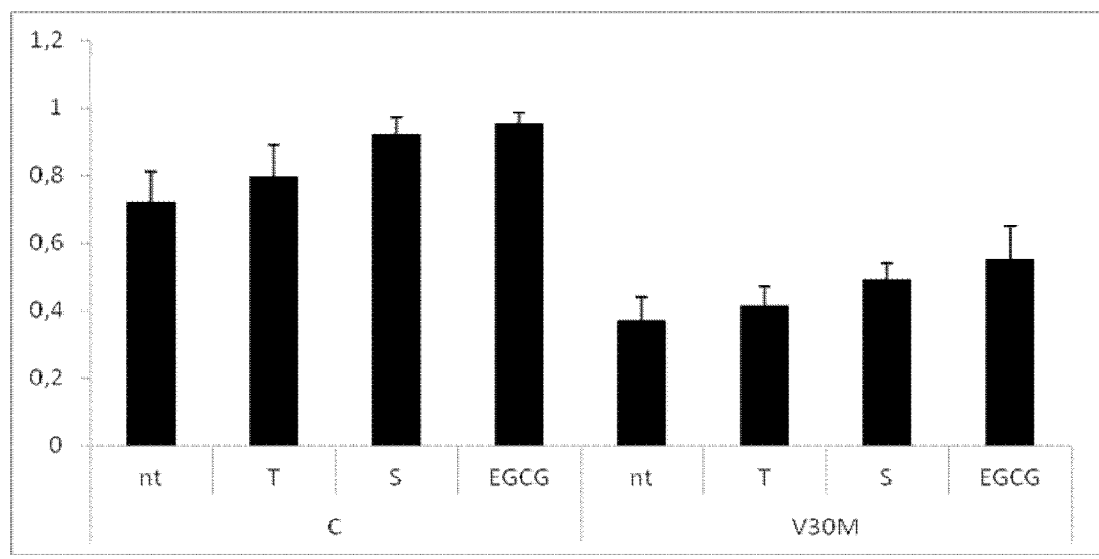
FIG. 2. TTR tetrameric stability in the presence of different compounds by IEF: Plasma from control individuals (C) and from familial amyloid polyneuropathy patients carrying V30M mutation (V30M) was treated with test compounds Tafamidis (T); tolcapone (S); epigallocatechin-3-gallate (EGCG) or left untreated (nt); and subjected to IEF under semidenaturing conditions as described in the text. The ratio of TTR tetramer/total TTR for each condition was calculated and represented as average+/−sem (standard error of the mean).

To evaluate the effect of the tested compounds on TTR tetramer resistance to dissociation, TTR stability was assessed by IEF in semi-denaturing conditions as previously described (Ferreira et al, 2009, *FEBS Lett*, vol. 583, p. 3569-76). Samples were prepared as follows: 30 μL of human plasma from controls and TTR V30M carriers were incubated with 5 μl of 10 mM solution of test compounds and control (EGCG) compounds overnight at 4° C. followed by a 1 h incubation at RT. The preparations were subjected to native PAGE (5% acrylamide) and the gel band containing TTR was excised and applied to an IEF gel (5% acrylamide). IEF was carried out in semi-denaturing conditions (4 M urea), containing 5% (v/v) ampholytes pH 4-6.5 (GE Healthcare), at 1200 V for 6 hours. Proteins were stained with Coomassie Blue, the gels were scanned and subjected to densitometry using the ImageQuant program (HP Scanjet 4470c, Hewlett Packard). In the absence of any compound, plasma TTR presented a characteristic band pattern, composed of monomer, an oxidized monomer and several lower isoelectric point (pI) bands corresponding to different forms of tetramers. A total of 12 plasma samples (5 controls and 7 carriers TTR V30M) were analyzed in 3 IEF gels. For each treatment condition, a minimum of 4 samples from different donors were processed. The ratio of TTR tetramer over Total TTR (TTR tetramer+monomer) was calculated for each plasma sample and represented in FIG. 2. This ratio is normally higher for plasma from normal individuals than for the plasma from heterozygotic TTR V30M carriers plasma, as observed in FIG. 2. Treatment with tolcapone increases the amount of TTR tetramer over the monomeric forms compared to the non treated control plasmas of both normal or mutant TTR; and to a higher extent than tafamidis.

The increase of the tetramer/total TTR ratio induced by the treatment with test compounds was pooled for all samples and represented in Table 4 as % of stabilization. These values were calculated after normalizing the tetramer/total TTR ratio obtained for each sample, with the ratio obtained for the non-treated plasma of the corresponding individual donor as described below: % stabilization=100× ((ratio sample−ratio nt)/ratio nt). Where "ratio sample" is tetramer/total TTR ratio in the presence of compound; and "ratio nt" is tetramer/total TTR ratio of non-treated plasma from same donor.

TABLE 4

Stability of TTR tetramer in the presence of compounds

|  | % stabilization (average +/− sem) |
| --- | --- |
| Tolcapone | 29.9 +/− 7.64 |
| Tafamidis | 16.4 +/− 5.49 |
| EGCG | 51.26 +/− 14.21 |

Treatment with a TTR stabilizer such as tafamidis or tolcapone increases the ratio of tetramer over the monomeric forms. The results shown above clearly demonstrate that tolcapone presents a better stabilization effect on TTR tetramers than tafamidis.

Example 5: Cell Toxicity Assays

To evaluate TTR-induced cytotoxicity and the preventive effect of the tested compounds, Rat Schwannoma cells (RN22, obtained from American Type Cell Collection ATCC), 80% confluent cells in Dulbecco's minimal essential medium with 10% fetal bovine serum, were exposed for 24 hours to 2 μM of TTR Y78F oligomers. These oligomers were obtained by incubation of soluble TTR Y78F either in the absence or presence of a 10× molar excess (final concentration is 20 μM) of test compounds or control (EGCG) at 37° C. for 6 days. Then, cells were trypsinized and cell lysates were used for determination of caspase-3 activation with the CaspACE fluorimetric 96-well plate assay system (Sigma). Protein concentration in lysates was determined with the Bio-Rad protein assay kit.

Figure 3:
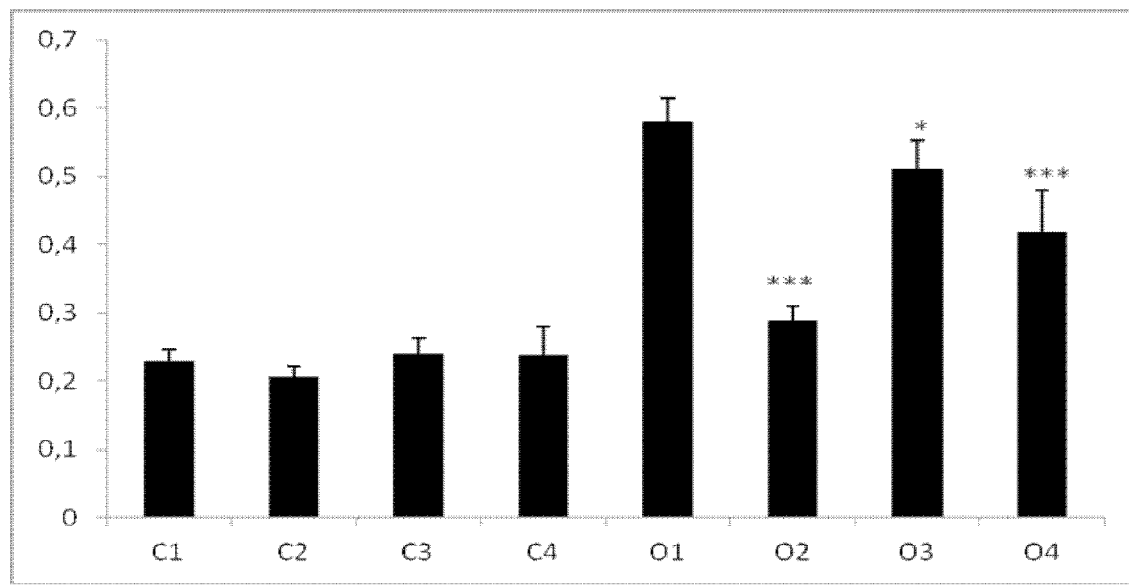
FIG. 3: Caspase-3 activation. Rat Schwannoma cells (RN22 cell line) were incubated 24 h in the absence or presence of TTR Y78F oligomers obtained in the absence or presence of tested compounds (at 20 µM). Activation of Caspase-3 was measured in cell lysates, and expressed as fluorescence/protein content. Samples: control cells (C1); Cells treated with EGCG (C2); Cells treated with tafamidis (C3); cells treated with tolcapone (C4); control cells treated with oligomer obtained in the absence of compounds (O1); cells treated with oligomer obtained in the presence of EGCG (O2); cells treated with oligomer obtained in the presence of tafamidis (O3); cells treated with oligomer obtained in the presence of tolcapone (O4). Results represent average of 4 replicates and standard deviation. Significant differences respect O1 control were calculated with T-student test: *: P<0.05; ***: P<0.005.

The results obtained for caspase 3 activity and protein quantification in each cell culture well are represented in FIG. 3. Extracellular addition of non-treated TTR Y78F oligomers (control, O1) increased intracellular levels of Caspase-3, and thus cell death. TTR Y78F oligomers obtained in the presence of compounds that inhibit the formation of toxic oligomeric species (O2-O4) caused lower levels of Caspase-3 activation in RN22 cells. The reduction of cell toxicity in the presence of compounds (expresed as 100−% relative to control O1) is shown in table 5. It can be observed that tolcapone showed a greater reduction of cell cytotoxicity (29%) as compared to tafamidis (12%).

TABLE 5

Reduction of cell toxicity in the presence of compounds

| | |
|---|---|
| Tolcapone | 29% |
| Tafamidis | 12% |
| EGCG | 50% |

Example 6: Fibril Disruption

To study the effect of the test compounds on TTR fibrils disruption, we used TTR pre-formed fibrils prepared by incubation of a filtered (0.2 μm filters) solution of TTR L55P (2 mg/ml in PBS≈3.6 μM) for 15 days at 37° C. Subsequently, the samples were incubated either in the absence (control) or presence of a 10× molar excess (36 μM) (final concentration) of the test compounds for 4 days at 37° C. The disruption effect was evaluated by Transmission Electron Microscopy (TEM) and Dynamic Light Scattering (DLS) as previously described (Ferreira et al, 2009, *FEBS Lett*, vol. 583, p. 3569-76).

Figure 4:
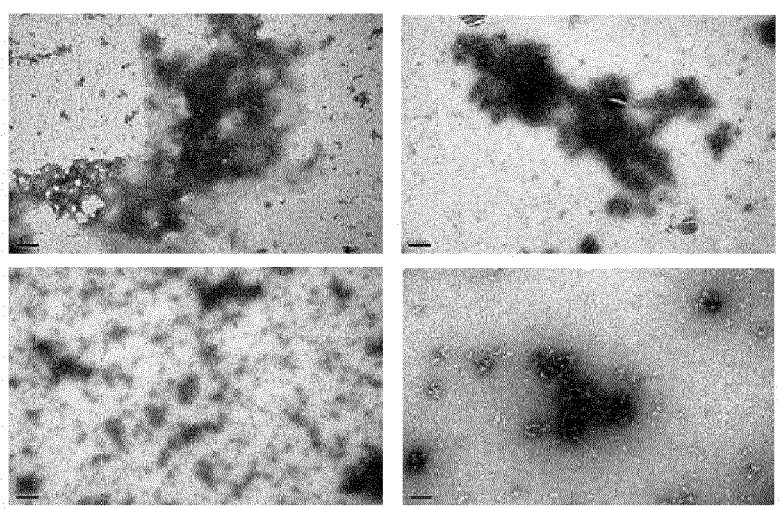
FIG. 4: Transmission Electron Microscopy analysis of preformed TTR fibrils after 4 days incubation with different compounds at 36 µM. From up left, clockwise: control, tafamidis, EGCG, Tolcapone.

It was observed that the control sample of TTR pre-formed fibrils (control) is mainly composed by big aggregates and fibrils (particles with a diameter higher than 1000 nm) and just a small amount of the protein is in soluble form (particles of 10 nm diameter). As the fibrils are being disrupted by the tested compounds the relative amount of big aggregates decrease and the small aggregates and soluble protein increase (see FIG. 4).

The fibril disruption activity was quantified from the DLS analysis as the relative intensity (%) of aggregates and soluble particles after 4 days treatment with 36 μM of compounds (table 6).

TABLE 6

DLS Analysis of TTR fibrils

| | relative intensity (%) | | |
|---|---|---|---|
| | Soluble particles (~10 nm) | Aggregates (~10-100 nm) | Aggregates (~1000 nm) |
| Control | 28.2 | — | 71.8 |
| tocalpone | 56.1 | 5.9 | 38 |
| Tafamidis | 35.2 | 6.7 | 58.1 |
| EGCG | 49.1 | 26.3 | 24.6 |

It can be observed that samples treated with tolcapone resulted in a higher amount of small aggregates and soluble proteins, thus exhibiting an important disruption activity. The results also show that tolcapone has a higher fibril disruption activity than tafamidis.

The results obtained by experiments 1-6 clearly demonstrate that tolcapone has a high inhibitory activity of the formation of TTR amyloid fibrils and such inhibitory activity is higher than tafamidis, which has been described for the treatment of FAP. Further, tolcapone can disrupt pre-formed TTR amyloid fibrils more effectively than tafamidis. Altogether, the results indicate that tolcapone can be effectively used as a a medicament for the treatment of all types of TTR-associated amyloidosis.

The invention claimed is:

1. A method for treating transthyretin (TTR)-associated amyloidosis comprising administering to a subject in need thereof a therapeutically effective amount of at least one catechol-O-methyltransferase (COMT) inhibitor, wherein the TTR gene of the subject contains at least one mutation compared to the wild type TTR gene.

2. The method of claim 1, wherein the mutation is selected from the group consisting of Y78F, V122I, V30M and L55P.

3. The method of claim 2, wherein the mutation is Y78F and the TTR-associated amyloidosis is familial amyloid polyneuropathy (FAP), familial amyloid cardiomyopathy (FAC), senile systematic amyloidosis and leptomeningeal amyloidosis.

4. The method of claim 2, wherein the mutation is V122I and the TTR-associated amyloidosis is familial amyloid cardiomyopathy (FAC).

5. The method of claim 1, wherein the COMT inhibitor is administered in an oral dosage form.

6. The method of claim 5, wherein the oral dosage form is selected from the group consisting of a tablet, pill, powder, capsule, sachet, liquid syrup, suspension and elixir.

7. The method of claim 1, wherein between about 1 mg/day and about 2,000 mg/day of the at least one COMT inhibitor is administered.

8. The method of claim 1, wherein the COMT inhibitor is selected from the group consisting of tolcapone, entacapone, nitecapone and pharmaceutically acceptable salts thereof.

9. The method of claim 8, wherein the COMT inhibitor is tolcapone.

10. The method of claim 1, further comprising administering an additional therapeutic agent selected from the group consisting of a benzoxazole derivative, iododiflusinal, diflunisal, resveratrol, tauroursodeoxycholic acid, doxycycline and epigallocatechin-3-gallate.

11. The method of claim 10, wherein the at least one COMT inhibitor and additional therapeutic agent are administered simultaneously or sequentially.

12. The method of claim 10, wherein the at least one COMT inhibitor and additional therapeutic agent are administered in two different compositions.

13. The method of claim 10, wherein the benzoxazole derivative is tafamidis.

14. The method of claim 10, wherein the COMT inhibitor is tolcapone and the additional therapeutic agent is a benzoxazole derivative.

15. The method of claim 14, wherein the tolcapone and tafamidis are administered in two different compositions.

16. The method of claim 15, wherein the tolcapone and tafamidis are administered simultaneously or sequentially.

* * * * *